United States Patent [19]

Merz

[11] Patent Number: 5,810,759
[45] Date of Patent: Sep. 22, 1998

[54] CONTROL SYSTEM FOR REGULATING GAS EXCHANGE IN EXTRACOPOREAL CIRCULATION

[75] Inventor: Scott I. Merz, Ann Arbor, Mich.

[73] Assignee: Michigan Critical Care Consultants, Inc., Ann Arbor, Mich.

[21] Appl. No.: 826,280

[22] Filed: Mar. 27, 1997

[51] Int. Cl.[6] ............................................ A61M 37/00
[52] U.S. Cl. .......................... 604/4; 604/50; 604/26; 422/44
[58] Field of Search ........................ 604/4–6, 50, 26; 422/44–45

[56] References Cited

U.S. PATENT DOCUMENTS

| | | | |
|---|---|---|---|
| 4,445,500 | 5/1984 | Osterholm | 128/1 |
| 4,445,886 | 5/1984 | Osterholm | 128/1 |
| 4,686,085 | 8/1987 | Osterholm . | |
| 4,734,184 | 3/1988 | Burleigh et al. | 204/409 |
| 4,786,394 | 11/1988 | Enzer et al. | 204/401 |
| 4,844,871 | 7/1989 | Polaschegg | 422/81 |
| 4,871,439 | 10/1989 | Enzer et al. | 204/401 |
| 5,614,378 | 3/1997 | Yang et al. | 435/41 |

Primary Examiner—John G. Weiss
Assistant Examiner—Ki Yong O
Attorney, Agent, or Firm—Harness, Dickey & Pierce, P.L.C.

[57] ABSTRACT

A control system for regulating oxygen and carbon dioxide concentrations of blood in an ECLS circuit connected to a patient. The control system includes a gas analyzer that determines the concentrations of carbon dioxide in the blood being withdrawn from the patient and of the oxygen in blood being returned to the patient. The analyzer provides concentration signals corresponding to these concentrations to a system controller. The system controller is also inputted with setpoint values for these concentrations. Utilizing control algorithm, the system controller calculates gas flow control and blood flow control signals based on the differences of the concentration signals and the setpoint values. A gas flow controller coupled to the system controller receives the gas flow control signal provides gas from a gas source to the ECLS circuit at a predetermined rate in response thereto. The blood flow control signal is communicated to a pump whose operating speed is the adjusted according to the blood flow control signal so as to control the blood flow rate through the ECLS circuit. As a result, the concentrations of carbon dioxide in the blood being withdrawn from the patient and of the oxygen in blood being returned to the patient are adjusted so as to approach the setpoint values thereof.

40 Claims, 6 Drawing Sheets

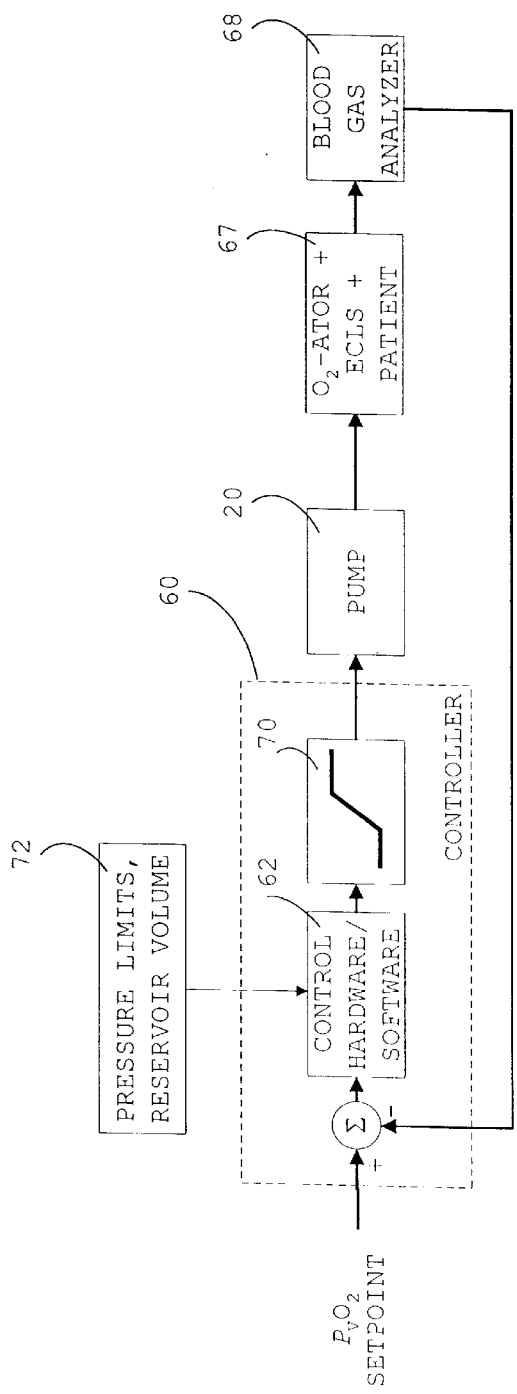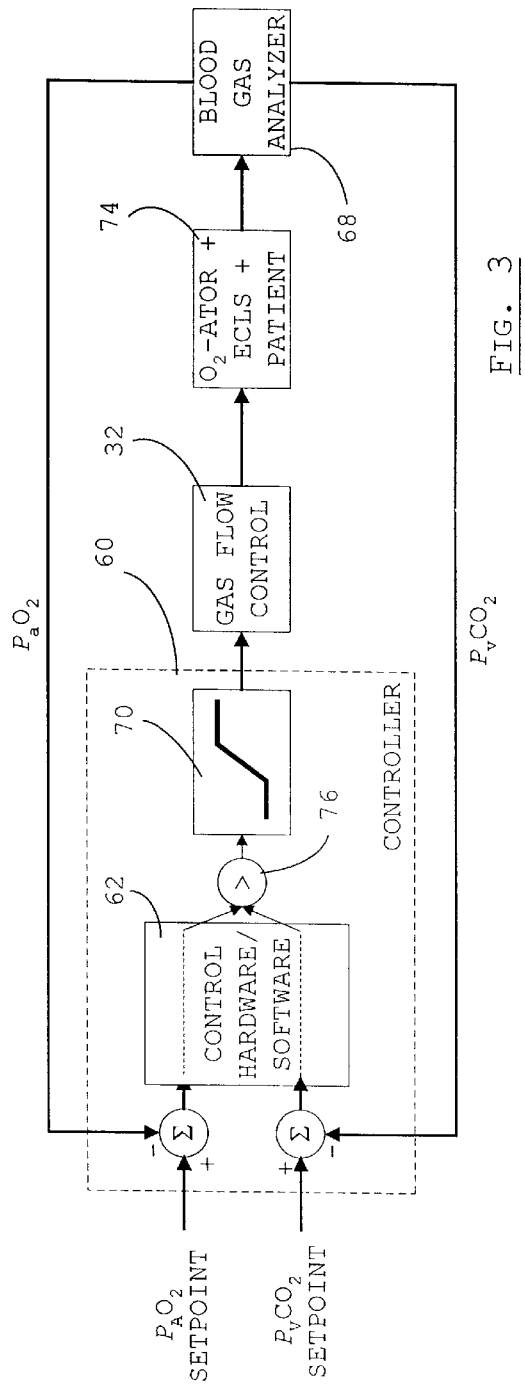

CONTROL SYSTEM FOR REGULATING GAS EXCHANGE IN EXTRACOPOREAL CIRCULATION

BACKGROUND OF THE INVENTION

1. Field of the Invention

The present invention relates to extracorporeal circulation and more particularly to a control system for regulating the gas exchange of oxygen ($O_2$) and carbon dioxide ($CO_2$) during extracorporeal circulation.

2. Description of the Prior Art

In the process of metabolism, a person consumes oxygen and produces carbon dioxide that must be removed from the body. In a healthy person, oxygen is transferred from the atmosphere to the blood across the lungs, and carbon dioxide diffuses from the blood to the lungs where it is expelled through exhalation. Pumped by the heart, blood transports the oxygen to and carbon dioxide from the body tissues. The efficacy of the transport of gases to and from body tissues and of the transfer of gases between a person's blood and the atmosphere is reflected by the concentration of oxygen and carbon dioxide at various points in the arterial and venous circulation. For example, a decrease in patient's metabolic rate, a decrease in the output of the patient's heart, or a decreases in the oxygen being supplied to the patient's lungs will all affect the concentrations of oxygen ad carbon dioxide in the patient's circulatory system. If the transport or transfer of gases is incompatible with life, extracorporeal life support (ECLS) may be used to supplement these processes. ECLS systems, sometimes referred to as heart-lung machines, are most often used for temporary cardiopulmonary support during by-pass surgery, during emergency resuscitations, and in situations requiring prolonged support (for as long as a month) such as during recovery from a condition that compromises cardiopulmonary functions.

Historically, gas exchange in ECLS has been controlled by a technician (perfusionist) who makes manual, ad hock changes to the ECLS system based on discrete or continuous measurements of venous and/or arterial blood gas concentrations. In addition to controlling operation of the ECLS system, the perfusionist is further responsible for anticipating and trouble shooting failures of the components of the ECLS system. The most common parameters adjusted by the perfusionist include the blood flow rate, the gas flow rate and composition of the gas being supplied to the gas exchange device, typically an oxygenator, of the ECLS system. These adjustments, however, only permit a limited range of control over the exchange of gases.

The adequacy of cardiorespiratory support provided by ECLS is quantified by several parameters, such as the venous and arterial blood gas chemistries, the blood pressure in the ECLS circuit and the blood pressure in the patient's circulatory system. Based on these measurements, the perfusionist will makes changes to the ECLS system.

Oxygen delivery by an ECLS system to the patient is the product of ECLS blood flow and the difference between the oxygen content of the blood being returned to the patient and that being drained from the patient. Carbon dioxide removal in an ECLS system is the product of ECLS blood flow and the difference between the carbon dioxide content of the blood being drained from the patient and that being returned to the patient. Oxygen delivery and carbon dioxide removal can therefore be controlled by controlling the ECLS blood flow and/or the oxygen content of the infused blood.

Oxygen delivery and carbon dioxide removal by an ECLS system is further determined by the gas exchange properties of the oxygenator used in the ECLS system. Oxygenators are designed with a transfer membrane having sufficient surface area to fully oxygenate blood, up to a specified flow rate, so long as a minimum ratio of blood flow to gas flow is maintained. The concentrations of the oxygen and carbon dioxide in the gas supplied to the oxygenator therefore determine the rate at which the gases are exchanged between the supply gas in the oxygenator and the blood. The flow rate of the supply gas in the oxygenator, relative to the flow rate of blood in the oxygenator, will therefore also affect the exchange of gases.

In addition to conducting gas exchange, ECLS systems often also provide blood flow and blood pressure support to the patient. In these cases, the flow of blood through the ECLS system must be sufficient to fully provide for gas exchange while still being sufficient to maintain the desired pressure in the patient's circulation. In certain situations, the blood flow in the ECLS system will need to be increased even though gas exchange is sufficient.

An additional and equally important responsibility of the perfusionist is controlling the ECLS system while the patient is being removed or weaned from support. Support is typically no longer needed when there is an improvement in the patient's condition or when surgery has been completed. In some cases, weaning may be a gradual process lasting several hours. In other cases, weaning may last several days. In the latter variety of cases, a manual system is both impractical and inefficient.

Obviously, automated control of an ECLS system would make management of the ECLS system more efficient since the system could more closely match the gas exchange needs of the patient without the constant attention of a perfusionist and the potential for human error. Additionally, an automated system eliminates the problems associated with long term weaning of a patient off of ECLS support since the continuous presence of a perfusionist is not be needed.

Implementing automatic control of ECLS gas exchange requires intimate knowledge of the relative influences of various system parameters on oxygen delivery and carbon dioxide removal, as generally discussed above. To date, there has only been limited application of automated ECLS control systems. When employed, these systems have been limited to only controlling the temperature of the blood, the blood pressure, or the regulation of blood flow. A system which automatically controls the delivery of oxygen and the removal carbon dioxide by adjusting blood flow rate, while maintaining adequate blood pressure in the system, has not been previously proposed or seen. Clearly, a need for such a system exists.

It is therefore the principal object of the present invention to fulfill that need by providing an ECLS system which automatically controls the delivery of oxygen and the removal carbon dioxide by adjusting blood flow rate, while maintaining adequate blood pressure in the system.

Another object of the present invention is to provide an ECLS system which is suitable for short term usage, both the long term care of patients and the long term weaning of patients off of support, all with a minimal amount of involvement by a perfusionist or other technician.

SUMMARY OF THE INVENTION

In achieving the above and other objects, the present invention provides an automated ECLS system which robustly controls both oxygen delivery and carbon dioxide removal. Oxygen delivery and carbon dioxide removal are achieved by controlling both ECLS blood flow and the gas flow to the oxygenator based on the gas exchange requirements of the patient. These requirements are quantified by continuous blood gas chemistry measurements made in either the extracorporeal circuit, intravascularly, or noninvasively. The automated system has several important advantages over the current manually operated and automated systems. These advantages include the ability to simultaneously and optimally control several parameters, to make anticipatory changes in the ECLS system based on measurements of additional patient data, such as ventilator settings.

Generally two control loops are utilized in the present invention, an oxygen delivery control loop and a carbon dioxide removal control loop.

In the first of the above control loops, the user or perfusionist defines a setpoint for the partial pressure of oxygen in the blood being drained from the patient (preoxygenated blood). This setpoint is compared to a value measured by a blood gas analyzer of the ECLS system. Based on the setpoint and the measured value, a controller circulates and outputs a control signal to the pump speed controller. This control signal is based on an oxygen delivery control algorithm and the controller enforces user-defined limits for the pump speed. Additionally, the controller checks blood flow (to ensure that the blood pump is functioning) and determines the validity of the readings from blood gas analyzer. To maintain ECLS circuit blood pressures within safe limits, a second? control loop has overriding capabilities with respect to the first control loop.

In the second control loop., the user defines setpoints for the partial pressure of carbon dioxide in the blood being drained from the patient and for the partial pressure of oxygen in the blood being returned to the patient. Separate control algorithms calculate control signals based on the errors between or the comparison of the setpoint values and the measurements taken by the ECLS blood gas analyzer of the partial pressure of carbon dioxide in the drained blood and the partial pressure of the oxygen in the blood being returned to the patient. Based on the above errors, the controller then enforces the user-defined limits on gas flow by calculating and outputting a control signal to the gas flow controller. The user-defined setpoints are necessary to avoid the possibility of oxygenation being compromised at the expense of carbon dioxide removal. The controller also confirms the gas flow (that the gas flow control is operating correctly) and additionally confirms the reading from the gas flow analyzer.

Obviously, control over oxygen delivery and carbon dioxide removal is not independent, gas flow and blood flow both influence oxygen and carbon dioxide transfer. Furthermore, oxygenator characteristics do not allow simultaneous achievement of all combinations of oxygen and carbon dioxide transfer. Compromises were therefore required. In the control strategy of the present invention, less strict requirements were specified for carbon dioxide removal than for oxygen delivery because of the latter's priority with respect to life support. To ensure that physiological unsafe conditions were prevented, performance goals were defined as: 1) 5 mm Hg overshoot of setpoint to step disturbances; 2) setting time to within 5% of setpoint of less than four minutes for the partial pressure of oxygen in the drained blood and ten minutes for the partial pressure of carbon dioxide in the drained blood; and 3) steady state error of less than 5 mm Hg for the partial pressures of oxygen and carbon dioxide drained from the patient.

Additional benefits and advantages of the present invention will become apparent to those skilled in the art to which the present invention relates from the subsequent description of the preferred embodiment and the appended claims, taken in conjunction with the accompanying drawings.

BRIEF DESCRIPTION OF THE DRAWINGS

FIG. 2 is a block diagram of the control loop for the partial pressure of oxygen in the blood drained from the patient;

FIG. 3 is a block diagram of the control loop for the partial pressure of carbon dioxide in the blood drained from the patient;

DESCRIPTION OF THE PREFERRED EMBODIMENT(S)

Figure 1:
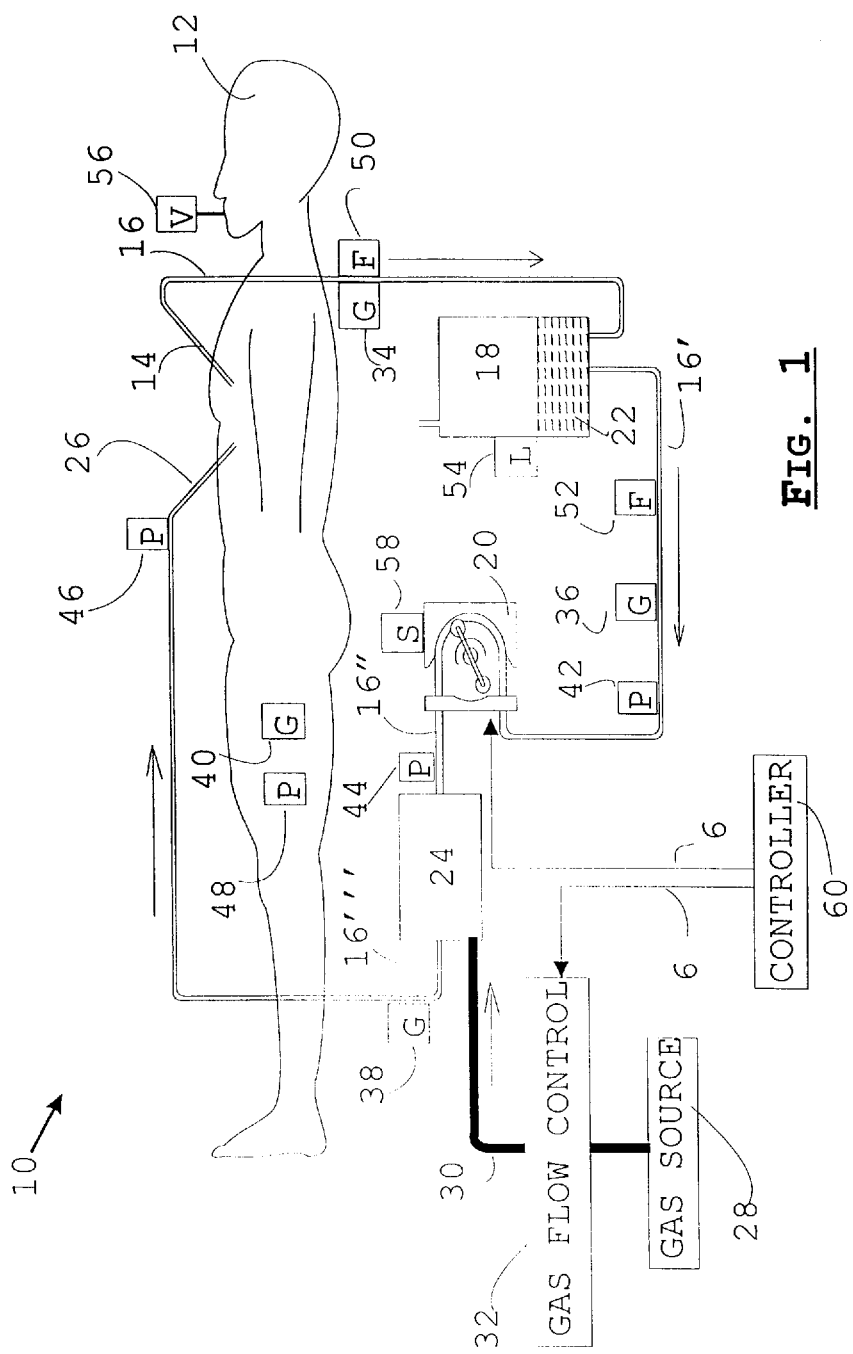
FIG. 1 is a diagrammatic illustration of an ECLS system embodying the principles of the present invention.

Referring now to the drawings, an ECLS system embodying the principles of the present invention is illustrated in FIG. 1 and generally designated at 10. ECLS itself is a procedure whereby a patient's 12 venous blood is drained through a venous cannula 14 into a circuit of plastic tubing 16 and sometimes into a reservoir 18 intended to store and possibly to filter the drained blood. A pump 20 draws the blood 22 from the reservoir 18 and pumps it through an oxygenator 24 (and possibly other blood treatment devices). After the oxygenator 24, the blood is oxygenated and returned to either the venous or arterial circulation through a return cannula 26. The oxygenator 24 is connected to a gas source 28 via a conduit 30. A well known gas flow control mechanism 32 for regulating the flow of gas from the gas source 28 through the oxygenator 24 is positioned in-line with the conduit 30.

Several sensors are included in the ECLS system 10. These sensors may include blood gas sensors 34, 36, 38, 40 respectively, in the path of blood drained from the patient 12, upstream from the oxygenator 24, downstream from the oxygenator 24 and/or invasive or noninvasive blood gas measurements of the patient's arterial and/or venous blood. Pressure sensors 42, 44, 46, 48 are placed upstream from the pump 20 and between the pump 20 and the oxygenator 24, at the return cannula 26, and at various points in the patient's arterial and/or venous circulation. Blood flow sensors 50, 52 are used to measure blood flow in the drainage line 16 upstream and/or downstream from the reservoir 18. A level sensor 54 is placed on the reservoir 18 to measure the volume of blood 22 in the reservoir 18 or to trigger an alarm if the level falls below a critical value. The patient's lungs are also ventilated with a mechanical ventilator 56 that has a variety of gas flow, gas concentration, volume and rate characteristics. A speed sensor 58 is used to monitor the rotational speed of the pump 20. Obviously, all or only some of the above sensors may be actually employed or provided depending on the particular design criteria of the ECLS system 10.

ECLS is used to provide partial or total gas exchange and/or circulatory support to a patient 12 during heart/lung surgery or in cases where ECLS support is required during the recovery of the patient 12 from any of several conditions that compromise cardiopulmonary function. In some cases, partial ECLS support is used to provide supplementary gas exchange to a patient who is capable of achieving limited gas exchange across the native lungs. For partial support, the venous cannula 14 is placed in the venous circulation of the patient 12 and a return path for venous blood is maintained.

An alternative of a two cannula system as shown in FIG. 1 is a single cannula, tidal flow ECLS system. In a tidal flow system, the arterial or return tubing 16''' is connected with a y-connector (not shown) to the venous cannula 14, thereby obviating the arterial or return cannula 26. Blood 22 is alternately drained from the patient 12 into the ECLS system 10 (drainage phase) and returned to the patient 12 from the ECLS system 10 (infusion phase). The previously described system 10 continuously circulates from the patient 12. The time required for one drainage phase and one infusion phase is referred to as the cycle period. With the tidal flow system, only a fraction of the patient's total blood volume is shifted back and forth between the patient 12 and the ECLS circuit 10. One of several clamping or valving mechanisms may be employed to direct the blood flow during the drainage and infusion phases. The duration and rate of the drainage and infusion phases of the process may be controlled by timers or may be triggered by pressure and/or volume measurements within the ECLS circuit 10 and/or patient 12. For example, in a volume controlled system, volume is measured in reservoir 18 placed upstream (or downstream) from the pump 20. The drainage phase is initiated and continues until the volume in the reservoir 18 reaches a defined value. At that point, the infusion phase begins by draining blood from the reservoir 18 as its filling is halted. The infusion phase continues until the volume in the reservoir 18 reaches a lower limit upon which the drainage phase is again started. The cycle period can be adjusted either by changing the speed of the pump (thereby decreasing the time required for the infusion phase), or by changing the volume limits that define the beginning of each phase (thereby changing the volume shifted between the patient 12 and the ECLS system 10). Tidal flow extracorporeal circulation has been widely used in ECLS and in kidney dialysis, but has not been automatically controlled to adjust gas exchange.

The present invention provides for the automatic control of the ECLS system 10 as so far described. Generically, a control system includes a process and an additional system (the controller) for causing a desired response (the controlled output) of the process. The response of the process is influenced by an input (control signal) from the controller to the process. The controller is typically provided with a target value (set point) that represents the desired output of the process. The controlled output of the process may be a measurable variable that can be supplied to the controller through a feedback path to attain greater control through knowledge of the difference (error) between the set point and controlled output, as well as the history of the error. The combination of the process and controller is collectively termed a control loop. If feedback is used, the control loop is referred to as a closed loop controller, otherwise it referred to as an open loop controller. The performance of the controller is typically quantified by the amount that the controlled output exceeds the set point (overshoot) and the time (setting time) required for the controlled variable to remain within a given range from the set point following a disturbance or change to the input of the process or following a change in set point. The controller may include characteristics (control parameters) that the user can change and therefore tune the system to achieve the desired response of the controlled output. An adaptive controller includes means for automatically tuning the control parameters based on the history of the controlled output, the output of the controller, and/or the response of the controlled output to known inputs. The controller may be implemented by a mechanical or electrical system or may be defined as a mathematical algorithm implemented with a digital computer. The control system may also be designed to produce a single controlled output based on a single set point, or possibly to control multiple controlled outputs based on multiple set points. Multiple input/output systems can be controlled sequentially, where the result of varying one control signal is observed before another control signal is changed, or simultaneously, where multiple control signals are changed at the same time, or essentially the same time, that is, much faster than the response time of the process. Another technique in multiple parameter control is selector control, where one control signal controls more than one controlled output and selects one of the control signals based on a decision scheme.

The ECLS system 10 of the present invention incorporates automated controls of the blood flow to meet the supplementary oxygen requirements of the patient 12, as reflected quantitatively by measuring the oxygen concentration of blood 22 through a gas sensor 40 (e.g., pulse oximetry) located either intravascularly, noninvasively or in the ECLS circuit (gas sensor 34, 36, 38). The oxygen content of the blood 22 may be measured by measuring both oxyhemoglobin saturation and partial pressure of oxygen or it may be approximated by measuring one of those two values and using known relationships between the measured value and oxygen content. The ECLS system 10 of the present invention may also be provided with means to simultaneously control the oxygen delivery and arterial blood pressure, while assuring that blood pressures within the ECLS circuit are within a safe range.

While fully discussed and illustrated as a continuous flow system, the control of blood flow in the present ECLS system 10 may also be accomplished in a tidal flow arrangement, as generally described above. In the tidal flow system, a controller adjusts the rate at which blood is shifted between the ECLS system 10 and the patient. Control of blood flow in a tidal flow arrangement is accomplished by adjusting the speed of the pump 20 or by adjusting the frequency at which the system switches between the drainage and infusion phases.

In addition to control of blood flow, the present invention 10 controls the flow rate of gas (typically 100% oxygen or a pre-mixed blend of oxygen, carbon dioxide and/or nitrogen) from the gas source 28 to and through the oxygenator 24 so as to meet the supplementary carbon dioxide removal requirements of the patient 12 as reflected quantitatively by the carbon dioxide concentration of the blood 22 drained into the ECLS system 10 or measured intravascularly or noninvasively.

Control of oxygen delivery and carbon dioxide removal as described herein can be used to adapt to the gas exchange requirements of the patient 12. Alternatively, the controller 60 can be used to maintain a desired level of oxygen delivery and carbon dioxide removal as specified by the user as a setpoint. As mentioned above, oxygen delivery is measured as the difference between the oxygen content of blood 22 drained from and that returned to the patient. Carbon dioxide removal can be determined from the difference in carbon dioxide concentrations between drained and infused blood or by measuring the partial pressure of carbon dioxide (PCO2) in the gas in inlet and exhaust of the oxygenator 24.

When control of the blood flow and gas flow works in concert, the system 10 ensures that control of one parameter does not compromise the ability to control the other parameter. For example, gas flow may be decreased by the controller 60 due to a falling PCO2. Below a certain level, however, gas flow will be insufficient to fully oxygenate the blood 22 leaving the oxygenator. The controller 60 must consider the post oxygenator 18 oxygen concentrations and sacrifice some control over PCO2 to ensure that blood 22 returned to the patient 12 is fully oxygenated. The present invention can use a model of gas exchange in the oxygenator 18 to optimize the simultaneous control of both oxygen and carbon dioxide.

Several variations on the degree of automation are possible with the present invention. The user has the option to control both blood flow and/or gas flow automatically or manually. Alternatively, one of these control outputs can be regulated based on the other; for example, gas flow can be made to adjust automatically to a constant (k) times the measured blood flow. The controller 60 can also be an adaptive controller that changes control characteristics according to various parameters such as blood flow, blood temperature, gas flow, or blood pressure. For example, the response rate of the blood gas measurements in the ECLS circuit is dependent on the blood flow rate because the blood flow rate determines how quickly the blood 22 reaches the blood gas sensors 34, 36, 38, 40. By varying the control parameters of the blood pump 20 according to the measured gas concentrations in blood flow, performance may be improved. The various control schemes of the controller 60 can also be self-turning, based either on adaption to control history or by generating patterns in the control output that can help to discern the dynamic characteristics of the process under control. The control schemes of the controller 60 can be derived using mathematical or logical algorithms (implemented in a digital form or effected using electrical and/or mechanical means) that produce an output or control signal in response to system data.

Based on the above, it can be seen that the novel aspects of the present invention include: 1) control of oxygen delivery by adjusting blood flow in an ECLS circuit, while simultaneously controlling pressure and/or blood flow within the circuit and/or the patient 12; 2) control as above where the parameters for control of the blood flow vary with blood flow; 3) control as above where the controller 60 adjusts gas flow through the oxygenator 24 based on a defined relationship between measured blood flow and measured gas flow; 4) a control system 10 that provides means for control as above and for control of carbon dioxide removal by adjusting the flow rate of gas through the oxygenator (the system 10 is provided with a means of overriding automatic control of one or both blood flow and gas flow and has the ability to recognize certain system malfunctions, subsequently alarm and automatically revert from automatic control to a constant controlled variable output); 5) control as above where the ECLS circuit is in a tidal flow arrangement, and the controller adjusts the speed of the pump to vary gas exchange; 6) control as above where the ECLS circuit is in a tidal flow arrangement, and the controller adjusts the drainage and infusion times to vary gas exchange (drainage and infusion phases being switched based on timers, and the controller varying the time of the drainage and infusion phases to change the cycle period); 7) control as above where the ECLS circuit is in a tidal flow arrangement, and the controller adjusts the drainage and infusion times to vary gas exchange (drainage and infusion phases being switched based on pressures measured within the ECLS circuit and the controller 60 varying the pressure limits to change the cycle period); 8) control as above where the ECLS circuit is in a tidal flow arrangement, and the controller adjusts the drainage and infusion times to vary gas exchange (drainage and infusion phases being switched based on the volume of blood shifted to the ECLS circuit and the controller varying the volume limits to change the cycle period); 9) control as above where the user defines set points for blood gas concentrations in the blood drained into the ECLS system; 10) control as above where the user defines set points for blood gas concentrations measured intravascularly; 11) control as above wherein the user defines set points for gas concentrations measured indirectly (e.g., ventilator gas, transdermally, pulse oximetry); 12) control as above where the user defines set points for gas exchange (e.g., volume of oxygen delivered or carbon dioxide removed per unit time); 13) control as above where the oxygen delivery and carbon dioxide control loops function separately to achieve their respective set points; 14) control as above where the oxygen delivery and carbon dioxide control loops are combined into a multiparameter control scheme; 15) control as above where the oxygen delivery and carbon dioxide loops are designated according to a model of gas exchange in the oxygenator 24 and/or the patient 12; 16) control as above where the oxygen delivery and carbon dioxide control loops are combined into a multiparameter control scheme according to a model of gas exchange in the oxygenator 24 and/or the patient 12; 17) control as above where the oxygen delivery and carbon dioxide control loops include feed forward control, based on data received, for example, from a ventilator; 18) control as above where the system 10 is capable of weaning a patient 12 from extracorporeal support as the patient's condition improves; 19) control as above where the system 10 employs adaptive control techniques, for example to compensate for nonlinearities, differences between patients, and/or time-variance of the system; 20) control as above using a proportional plus integral plus derivative control; and 21) control as above using a fuzzy control and/or neural network technologies.

One realization of the present invention was constructed and tested. A host microcomputer (hereinafter "computer 60") was equipped with hardware and software to permit the acquisition of data, the calculation of control signals, and the output of those control signals to various elements of the ECLS circuit (collectively referred to as the controller 62).

Sensors (including the necessary signal conditioning hardware/software) as discussed above were incorporated into the ECLS circuit and electrical signals from the sensors were input to the data acquisition system on the computer 60. The sensors included continuous blood gas sensors 38 or 36, 34 (placed both downstream and upstream from the oxygenator 18), a blood flowmeter 50 or 52, and blood pressure sensors 42 and 44 placed upstream and downstream from the pump 20 and at various pints in communication with the patient's arterial and venous circulation. A gas flowmeter measured gas flow through the oxygenator 24.

The controlled outputs from the computer included a speed control signal supplied to the blood pump 20 over line 62 and a gas flow control signal provided over line 64 to the gas flow controller 32 to regulate the flow of gas through the oxygenator 24.

From the appropriate gas sensor 34 or 36 and 38, the controller 62 reads the partial pressure of oxygen 24 upstream (PvO2) from the oxygenator and downstream (PaO2) from the oxygenator 24. In response to these readings, the controller 62 adjusts the speed of the blood pump 20 (and hence the blood flow 24 through the ECLS circuit 11) in an attempt to attain the PvO2 set point as the actual PvO2 measured value. Additionally, the controller 62 also monitored pressures within the ECLS circuit 11 and the patient's circulation by pressure sensors 48 and 42. To ensure that the pressure within the ECLS circuit 11 upstream from the pump 20 was maintained within acceptable limits, selector control techniques were employed to override PvO2 control if necessary. As an alternative to PvO2 control, the system 10 enables a user to choose to control the speed of the pump 20 to maintain the desired oxyhemoglobin saturation of blood in either the ECLS circuit 11 or in the patient's venous or arterial circulation.

Concurrently with control of PvO2, the controller 62 also read the partial pressure of carbon dioxide upstream (PvCO2) from the oxygenator 24 via gas sensor 34 or 36 and according to calculated control signals for the gas flow control 32 so that the flow rate from the single gas source 28 (either 100% oxygen or a pre-mixed blend of oxygen and carbon dioxide) through the gas side of the oxygenator 24 is controlled. During PvCO2 control, the controller 62 also reads the partial pressure of the oxygen downstream (PaO2) of the oxygenator 24. If the PaO2 falls below an acceptable limit, the controller 62 employs selector control techniques to increase the gas flow thereby overriding the PvCO2 control if necessary.

Block diagrams of the PvO2 and PvCO2 control loops are respectively provided in FIGS. 2 and 3. As seen in the PvO2 control loop, the blood volume of the patient plus ECLS system, the gas exchange properties of the ECLS oxygenator, and oxygen delivery/consumption relationship of the patient, (designated by box 67) are all factors in determining the oxygen content of the patient's arterial and venous blood and the oxygen content of the blood at various points in the ECLS circuit 11. The oxygen content of blood in the patient's circulation and/or within the ECLS circuit is measured by a blood gas analyzer 68 (which incorporates the various gas sensors 34, 36, 38), and supplied as feedback information to the computer 60 and controller 62. The computer 60 and controller 62 also accepts a set point defined by the user for PvO2 and subtracts it from the value read by the blood gas analyzer 68 to obtain an error value. The control software of the controller 62 uses the error value and the history of the error value to calculate a control signal, which is translated to a voltage signal at 70 which is provided to the speed control of the blood pump 20. The controller 60 also receives additional information regarding the level of blood in the reservoir 18 and regarding the pressures from the pressure sensors 42 and 44 in the ECLS circuit 11 and the patient's circulation pressure sensor 48. This information is designated in box 72 to determine whether the calculated blood pump speed will possibly result in undesirable pressures in the ECLS circuit 11 or an unsafe volume in the reservoir 18. The pump speed determines the flow of blood between the patient and the ECLS circuit.

The block diagram of FIG. 3 is the control loop for regulating gas flow through the oxygenator 24. In this control loop, two sub-loops function together. * In the first, the user selects a set point or desired value for PvCO2. The controller reads the actual measured value from the blood gas analyzer and, based on the error and history of the error, calculates a control signal for the gas flow rate through the oxygenator. Simultaneously with the PvCO2 control, the controller compares the measured and desired (set point) value for PaO2 and calculates another control value for gas flow rate through the oxygenator. The controller then selects the greater of the two calculated control signals, converts it to volts, and outputs the control signal to the gas flow controller. The gas flow controller regulates the flow rate of gas supplied to the oxygenator. * In that the gas exchange properties of the oxygenator 24, the blood flow and volume characteristics of the ECLS circuit 11 and the patient's circulation, and oxygen delivery/consumption and carbon dioxide production/elimination by the patient 12 are factors that determine the resulting PvCO2 (and PaO2) value (generally designated at box 74), the blood gas analyzer 68 measures these values and provides them as feedback to the controller 62.

Figure 4:
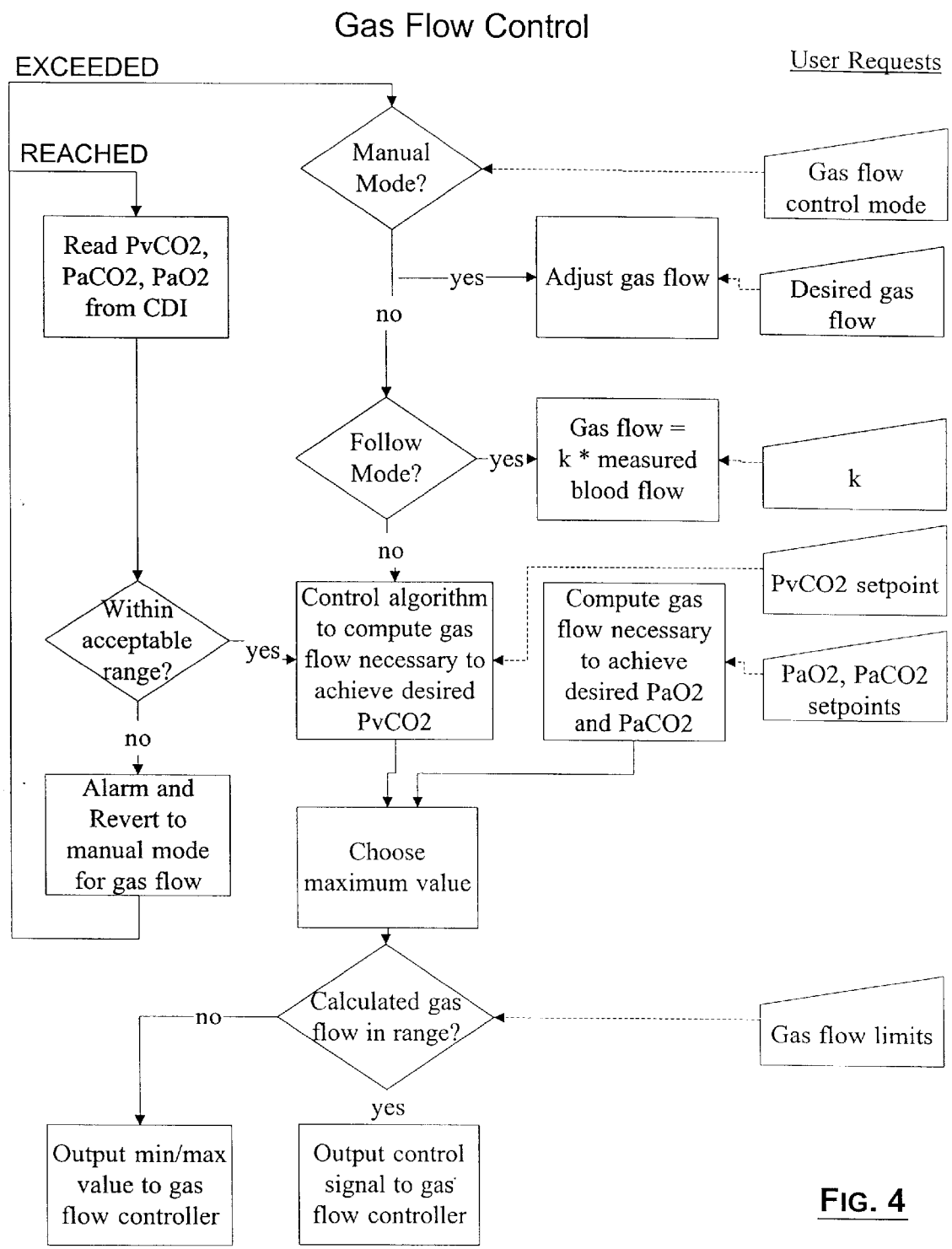
FIG. 4 is a block diagram of the algorithm for gas flow control.
Figure 5:
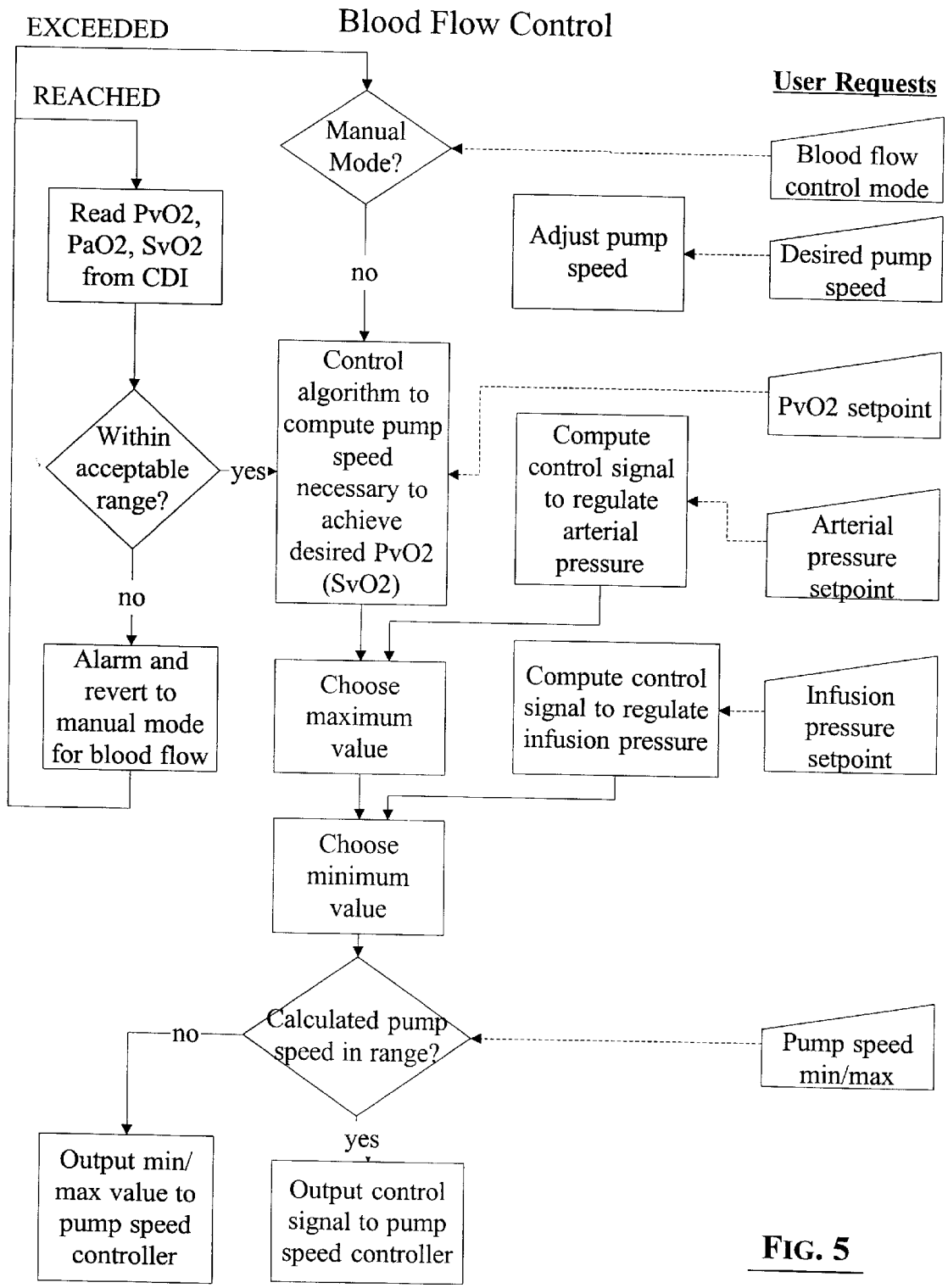
FIG. 5 is a block diagram of the blood gas flow.

With the ECLS system 10 of the present invention, the user is able to select one of several modes of system control. If desired, the controller 62 will simultaneously control the blood flow via the blood pump 20 and gas flow (via gas flow control 32) to the oxygenator, thereby controlling PvO2, ECLS circuit 11 pressures, patient blood pressures, PvCO2 and PaO2. Alternatively and as seen in FIGS. 4 and 5, the user can select to manually control the gas flow and/or blood flow to the to the oxygenator 24. The user could choose to control gas flow to the oxygenator 24 so it equaled a constant (k) times the measured blood flow in the ECLS circuit 11. The user further specifies minimum and maximum values or limits for the pump speed, the gas flow, PvO2, PvCO2, PaO2, PaCO2, infusion and arterial pressures, and the constant mentioned above. If limits are reached, an alarm is generated by branches of the gas flow and blood flow control algorithms of FIGS. 4 and 5. If the various limits were exceeded, the controller 62 would be caused to revert to manual control.

The control algorithms utilized by the controller 62 were proportional plus integral (PI) or proportional plus integral plus derivative (PID) routines. Tuning of the controller 62 was based on the open loop response of the system to a sudden change in set point. The controller 62 was tuned until the settling time to within 5% of setpoint was less than five minutes, with less than a 10% overshoot of the setpoint and less than 5% steady state error between the controlled variable and the setpoint.

The controller 62 used gain scheduling techniques to improve performance. Gain scheduling as used involved the adjustment of controller parameters depending on the pump speed or blood flow. This was because the time required for blood to travel between the ECLS circuit 11 to the patient 12 can then to the blood gas sensors 34, 36, 38 varied with blood flow. This variable delay changed the dynamic characteristics of the control system 10; hence, the controller 62 needs to adapt to changing conditions to maintain the desired performance. Where control parameters needed to be calculated, the control parameters were defined as either discrete or continuous functions of blood flow or pump speed.

In actual tests, sheep were anaesthetized, mechanically ventilated and instrumented to access the physiological stability of the present system 10. Relationships between the blood flow and the PvO2 and between the gas flow and the PvCO2 were molded by first order systems (time cost and less than 10 seconds) with time to delays typically less than five seconds, based on open loop step response. The dynamic responses of the continuous blood gas sensors 34, 36, 38 (system 300, CDI/3M, Minneapolis, Minn.) were modeled by first order transfer functions with time costs and equal to two minutes as determined with in vitro step response measurements. Accordingly, the time response of the entire system was assumed to be dominated by the blood gas sensors. The sampling time was six seconds, which is the maximum update rate of the in-line blood gas analyzer (CDI/3M, Tustin, Calif.). The gas flow controller (Aalborg Instruments and Controls, Inc., Monsey, N.Y.) calibrated for oxygen flows from 0–10 liters per minute. A passively filling roller pump (MC3, Inc., Ann Arbor, Mich.) regulates the blood flow. Blood flow is manually adjusted to the maximum possible value and gas flow is set to equal the blood flow. Mechanical ventilation will then decrease to a point where the animal was dependent on ACLS system 10 for a significant fraction of its gas exchange requirements. The control algorithms for PaO2 and PvCO2 were two grossly using the Ziegler Nichols method: under manual control, step changes of 25% full scale or made alternately in blood flow and gas flow, and resulting changes in PvO2 and PvCO2 were observed. The controller was further tuned by observing the closed lip response to sudden changes in the PvO2 and PvCO2 setpoints and adjusting the controller parameters to where acceptable responses were attained. By changing the ventilator settings, oxygen delivery and carbon dioxide removal from the sheep is altered and the ACLS system 10 of the present invention was used to maintain PvO2 and PvCO2 at the user defined setpoints.

Figure 6A:
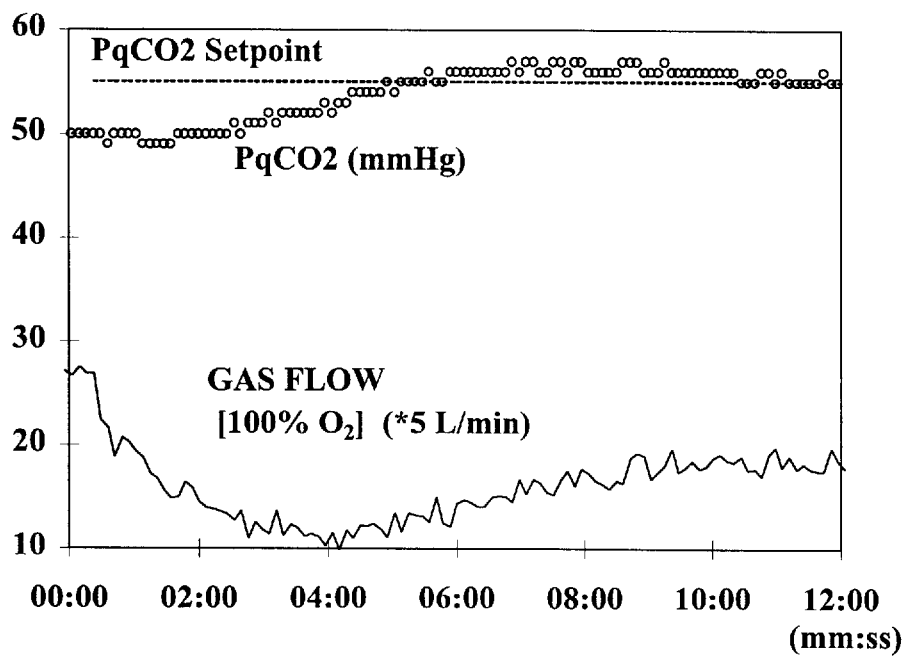
FIGS. 6a and 6b are graphs for the in vivo assessment of the ECLS control system.
Figure 6B:
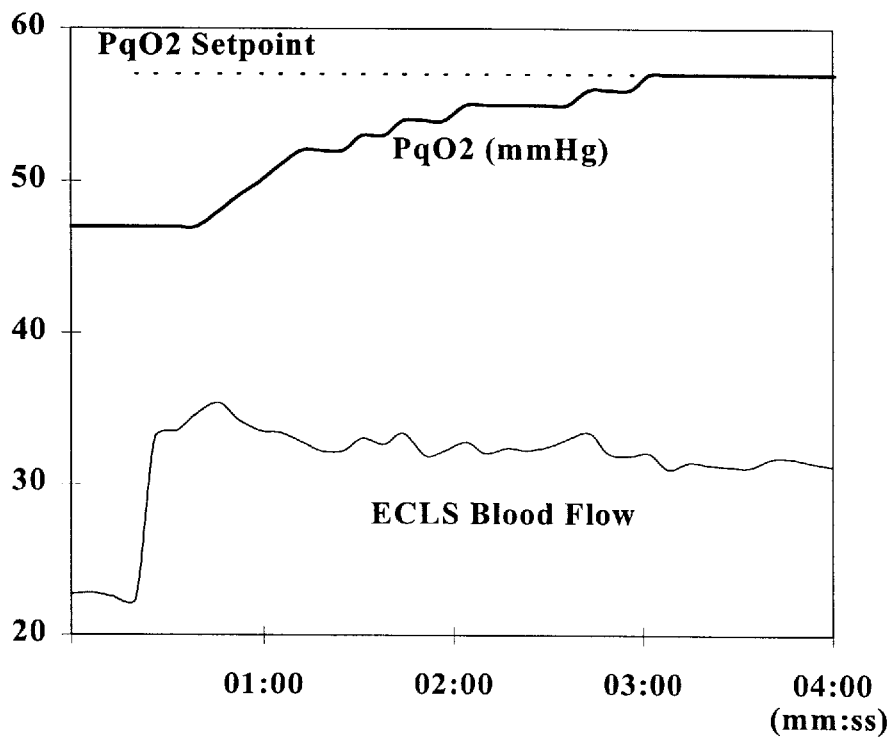
Figures 7A, 7B:
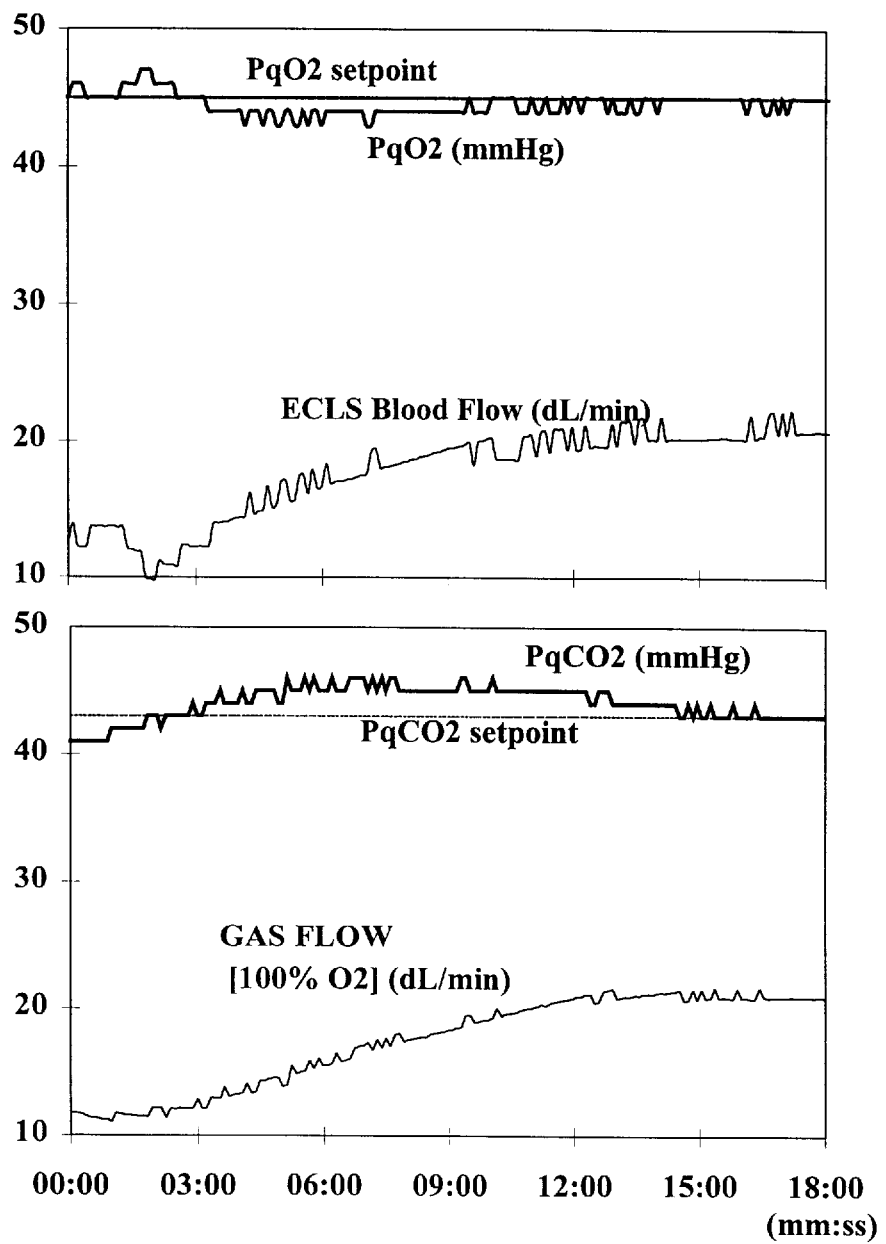
FIGS. 7a and 7b are graphs for the in vivo assessment of the delivered oxygen and removed carbon dioxide.

FIGS. 6a and 6b illustrate the tuning of the ACLS system 10 in an experiment using a 32 kilogram sheep placed on the system 10. The PvCO2 setpoint was stepped from 50–55 mmHg and it can be seen that the response of PvCO2 via the system 10 reached the setpoint in approximately five minutes with a minimum of overshoot and settled to the setpoint at around twelve minutes. In a change of the PvO2 setpoint, 47–57 mmHg, the PvO2 responds to the system via the controller 62 to the setpoint was achieved in approximately three minutes. In FIGS. 7a and 7b, the mechanical ventilator of the sheep was similar and the controller 62 of the system 10 increased blood flow and gas flow to compensate for the increased gas exchange requirements of the animal. Both the blood flow and gas flow (QG) were seen to increase respectively from 1.1–2.0 liters per minute and 1.1–2.1 liters per minute in response to a decrease in the mechanical ventilation from eight to two breaths per minute. PvO2 and PvCO2 were seen to remain within limits about the respective setpoints.

While the above description constitutes the preferred embodiment of the present invention, it will be appreciated that the invention is susceptible to modification, variation and change without departing from the proper scope and fair meaning of the accompanying claims.

I claim:

1. An apparatus for regulating oxygen and carbon dioxide transfer between an ECLS circuit and a patient, said apparatus comprising:
   gas analyzer means for determining gas exchange between the ECLS circuit and the patient relative to metabolic gas exchange requirements of the patient by measuring concentrations of carbon dioxde and oxygen in venous blood, said gas analyzer means providing concentration signals corresponding to said concentrations of carbon dioxide and of oxygen in venous blood;
   input means for inputting setpoint values for said concentrations of carbon dioxide and of oxygen in venous blood;
   a system controller coupled to said gas analyzer means and receiving said concentration signals therefrom, said system controller including calculation means for comparing said concentration signals with said setpoint values and calculating a gas flow control signal and a blood flow control signal therefrom;
   a pump for pumping blood through the ECLS circuit, said pump including speed control means for controlling operating speed of said pump and blood flow rate through the ECLS circuit, said speed control means coupled to said system controller, receiving said blood flow control signal therefrom, operating said pump at a predetermined speed in response to said blood flow control signal, and controlling said blood flow rate through the ECLS circuit;
   a gas flow controller coupled to said system controller and receiving said gas flow control signal therefrom, said gas flow controller providing gas from a gas source at a predetermined rate to the ECLS circuit in response to said gas flow control signal;
   whereby said concentrations of carbon dioxide and of oxygen in venous blood are adjusted so as to approach said setpoint values thereof.

2. An apparatus as set forth in claim 1 further comprising carbon dioxide override means for preventing concentrations of oxygen from being lowered to a level resulting in an insufficient delivery of oxygen from the ECLS circuit to the patient due to decreases in gas provided to the ECLS circuit in response to said gas flow control signal.

3. An apparatus as set forth in claim 2 wherein said carbon dioxide override means includes said gas analyzer means providing a concentration signal corresponding to oxygen in blood being returned to the patient.

4. An apparatus as set forth in claim 3 wherein said carbon dioxide override means further includes said input means inputting a setpoint value for said concentration of oxygen in blood being returned to the patient.

5. An apparatus as set forth in claim 4 wherein said carbon dioxide override means further includes said calculation means of said system controller comparing a difference in said concentration signal of oxygen in blood being returned to the patient and said setpoint value of oxygen in blood being returned to the patient to a difference in said concentration signal of carbon dioxide in blood being withdrawn from the patient and said setpoint value of carbon dioxide in blood being withdrawn from the patient, said system controller utilizing said differences to calculate two gas flow control signals, the larger of said gas flow control signals being provided to said gas flow controller so as to provide gas from said gas source at a predetermined rate to the ECLS circuit.

6. An apparatus as set forth in claim 1 further comprising oxygen override means for preventing blood pressures in the ECLS circuit from being increased to a pressure sufficient to damage the ECLS circuit due to increases in blood flow rate through the ECLS circuit in response to said blood flow control signal and blood pressures in the patient from being lowered to an insufficient pressure for ECLS of the patient due to decreases in blood flow rate through the ECLS circuit in response to said blood flow control signal.

7. An apparatus as set forth in claim 6 wherein said oxygen override means includes said input means inputting a setpoint range limit for blood pressures in the ECLS circuit and the patient.

8. An apparatus as set forth in claim 7 wherein said oxygen override means further includes pressure sensor means for monitoring blood pressures in the ECLS circuit and the patient and also for providing pressure signals to said system controller, said calculation means of said system controller comparing said pressure signals with said setpoint range limits for blood pressures in the ECLS circuit and the patient and outputting an override blood flow control signal to said speed control means if said pressure signals are not within said setpoint range limits.

9. An apparatus as set forth in claim 6 wherein said oxygen override means is also for preventing blood levels in a reservoir of the ECLS circuit from being lowered to an insufficient level for ECLS of the patient due to increase in blood flow rate through the ECLS circuit from the reservoir in response to said blood flow control signal.

10. An apparatus as set forth in claim 9 wherein said oxygen override means includes said input means inputting a minimum reservoir volume limit for blood levels in the reservoir of the ECLS circuit.

11. An apparatus as set forth in claim 10 wherein said oxygen override means further includes level sensor means for monitoring blood levels in reservoir of the ECLS circuit and for level signals to said system controller, said calculation means of said system controller comparing said level signals with said minimum blood level limit and outputting an override blood flow control signal to said speed control means if said level signal is not above said minimum blood level limit.

12. An apparatus as set forth in claim 1 further comprising oxygen override means for preventing blood levels in a reservoir of the ECLS circuit from being lowered to an insufficient level for ECLS of the patient due to increase in blood flow rate through the ECLS circuit from the reservoir in response to said blood flow control signal.

13. An apparatus as set forth in claim 12 wherein said oxygen override means includes said input means inputting a minimum reservoir volume limit for blood levels in the reservoir of the ECLS circuit.

14. An apparatus as set forth in claim 13 wherein said oxygen override means further includes level sensor means for monitoring blood levels in reservoir of the ECLS circuit and for level signals to said system controller, said calculation means of said system controller comparing said level signals with said minimum blood level limit and outputting an override blood flow control signal to said speed control means if said level signal is not above said minimum blood level limit.

15. An apparatus as set forth in claim 1 wherein said apparatus includes means for operating the ECLS circuit in a tidal flow mode of operation.

16. An apparatus as set forth in claim 1 wherein said apparatus includes means for operating the ECLS circuit in a continuous mode of operation.

17. An apparatus as set forth in claim 1 wherein said calculation means calculates said gas flow control signal as a constant times blood flow rate.

18. An apparatus as set forth in claim 1 wherein concentrations in said venous blood are measured while said venous blood is in the ECLS circuit.

19. An apparatus as set forth in claim 1 wherein concentrations in said venous blood are measured intravascularly.

20. An apparatus as set forth in claim 1 wherein said concentrations in said venous blood are measured non-invasively.

21. A method for regulating oxygen and carbon dioxide transfer between an ECLS circuit and to a patient, said method comprising the steps of:
analyzing gas exchange between the ECLS circuit and the patient relative to metabolic gas exchange requirements of the patient by measuring concentrations of carbon dioxide and of oxygen in venous blood;
producing concentration signals corresponding to the concentrations of carbon dioxide and of oxygen in venous blood;
initializing setpoint values for the concentrations of carbon dioxide and of oxygen in venous blood, said setpoint values being initialized into a microprocessor based controller a control algorithm therein;
providing said concentration signals to the controller;
comparing the concentration signals with the setpoint values and using said control algorithm to calculating a gas flow control signal and a blood flow control signal;
adjusting gas flow from a gas source to a predetermined rate based on the gas flow control signal and providing the gas flow to a component in the ECLS circuit;
adjusting operating speed of a pump in the ECLS circuit to achieve a predetermined blood flow rate based on the blood flow control signal;
whereby the concentrations of carbon dioxide and of oxygen in venous blood are adjusted so as to approach the setpoint values thereof.

22. The method of claim 21 further comprising the step of preventing the concentration of oxygen in blood being returned to the patient from being lowered to a level resulting in an insufficient delivery of oxygen from the ECLS to the patient as a result of a decrease in the flow rate of gas being provided to the ECLS circuit in response to the gas flow control signal.

23. The method of claim 22 wherein said preventing step includes analyzing gas concentrations of oxygen in the blood being returned to the patient and providing a concentration signal to the controller corresponding to the concentration of the oxygen in the blood being returned to the patient.

24. The method of claim 23 wherein said preventing step further includes inputting into the controller a setpoint value for the concentration of the oxygen in the blood being returned to the patient.

25. The method of claim 24 wherein said preventing step includes the controller comparing a difference in the concentration signal of oxygen in the blood being returned to the patient and the setpoint value of oxygen in the blood being returned to the patient to a difference in the concentration signal of carbon dioxide in the blood being withdrawn from the patient and the setpoint value of carbon dioxide in the blood being withdrawn from the patient, the controller utilizing the differences to calculate two gas flow control signals, providing the larger of said gas control signals to said gas flow controller.

26. The method of claim 21 further comprising the step preventing blood pressures in the ECLS circuit from being increased a pressure sufficient to damage the ECLS circuit due to increases in blood flow through the ECLS circuit in response to said blood flow control signal and for preventing blood pressures in the patient from being lowered to an insufficient pressure for ECLS of the patient due to decreases in blood flow rate through the ECLS circuit in response to the blood flow control signal.

27. The method of claim 26 wherein said preventing step includes inputting a setpoint range limit for blood pressures in the ECLS circuit and the patient.

28. The method of claim 27 wherein said preventing step further includes the step of monitoring blood pressures in the ECLS circuit and the patient and providing pressure signals to the controller based thereon, the controller comparing the pressure signals with the setpoint range limit for the blood pressures in the ECLS circuit and in the patient and outputting an override blood flow control signal to the pump if the pressure signals are not within the setpoint range limit.

29. The method of claim 26 further comprising the step of preventing blood levels in a reservoir of the ECLS circuit from being lowered to an insufficient level for ECLS of the patient due to an increase in the blood flow rate through the ECLS circuit from the reservoir in response to the blood flow control signal.

30. The method of claim 29 wherein the preventing step further includes the step of inputting into the controller a minimum reservoir volume limit for blood levels in the reservoir of the ECLS circuit.

31. The method of claim 30 wherein the preventing step further includes the step of monitoring blood levels in the reservoir of the ECLS circuit and providing level signals to the controller, the controller comparing the level signals with the minimum blood level limit and outputting an override blood flow control signal to the pump when the level signal is not above the minimum blood level limit.

32. The method of claim 21 further comprising the step of preventing blood levels in a reservoir of the ECLS circuit from being lowered to an insufficient level for ECLS of the patient due to an increase in the blood flow rate through the ECLS circuit from the reservoir in response to the blood flow control signal.

33. The method of claim 32 wherein the preventing step further includes the step of inputting into the controller a minimum reservoir volume limit for blood levels in the reservoir of the ECLS circuit.

34. The method of claim 33 wherein the preventing step further includes the step of monitoring blood levels in the reservoir of the ECLS circuit and providing level signals to the controller, the controller comparing the level signals with the minimum blood level limit and outputting a minimum blood flow control signal to the pump when the level signal is not above the minimum blood level limit.

35. The method of claim 21 comprising the step of operating the ECLS circuit in a tidal flow mode of operation.

36. The method of claim 21 comprising the step of operating the ECLS circuit in a continuous flow mode of operation.

37. The method of claim 21 comprising the step of calculating said gas flow control signals as a constant times blood flow rate.

38. The method of claim 21 comprising the step of measuring the concentrations of the venous blood in the ECLS circuit.

39. The method of claim 21 comprising the step of measuring the concentrations of venous blood intravenously.

40. The method of claim 21 comprising the step of measuring the concentrations of venous blood non-invasively.

* * * * *

UNITED STATES PATENT AND TRADEMARK OFFICE
CERTIFICATE OF CORRECTION

PATENT NO. : 5,810,759
DATED : September 22, 1998
INVENTOR(S) : Scott I. Merz

It is certified that error appears in the above-identified patent and that said Letters Patent is hereby corrected as shown below:

On the title page, item [54] and in column 1, line 2,.

In the title, delete "EXTRACORPOREAL" and insert --EXTRACORPOREAL--.

In the Abstract, line 18, after "speed is", delete "the".

In column 1, line 26, delete "ad" and insert --and--.

In column 1, line 38, delete "hock" and insert --hoc--.

In column 2, line 36, after "not", delete "b".

In column 3, line 26, after "from", insert --the--.

In column 3, line 27, after "second", delete "?".

In column 3, line 29, after "loop", delete "," (first occurrence).

UNITED STATES PATENT AND TRADEMARK OFFICE
CERTIFICATE OF CORRECTION

PATENT NO. : 5,810,759
DATED : September 22, 1998
INVENTOR(S) : Scott I. Merz

It is certified that error appears in the above-identified patent and that said Letters Patent is hereby corrected as shown below:

In column 5, line 8, after "16'", delete """.

In column 9, line 57, after "together.", delete "***".

In column 10, line 2, after "oxygenator" delete "***".

In column 10, line 18, after "flow" delete "to the" (first occurrence).

In column 10, line 44, delete "can" and insert ---and---.

Signed and Sealed this

Twenty-ninth Day of June, 1999

Attest:

Q. TODD DICKINSON

Attesting Officer

Acting Commissioner of Patents and Trademarks